(12) United States Patent
Toetsch et al.

(10) Patent No.: US 7,232,931 B2
(45) Date of Patent: Jun. 19, 2007

(54) METHOD FOR THE RHODIUM-CATALYZED HYDROFORMYLATION OF OLEFINS WITH REDUCTION OF RHODIUM LOSSES

(75) Inventors: Walter Toetsch, Marl (DE); Alfred Kaizik, Marl (DE); Hermann-Josef Schulte-Althoff, Haltern (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 10/511,280

(22) PCT Filed: Dec. 5, 2002

(86) PCT No.: PCT/EP02/13779

§ 371 (c)(1),
(2), (4) Date: Oct. 22, 2004

(87) PCT Pub. No.: WO03/095406

PCT Pub. Date: Nov. 20, 2003

(65) Prior Publication Data

US 2005/0182277 A1   Aug. 18, 2005

(30) Foreign Application Priority Data

May 10, 2002   (DE)   ................. 102 20 801

(51) Int. Cl.
*C07C 45/50* (2006.01)
*C07C 45/90* (2006.01)
(52) U.S. Cl. ............ 568/429; 568/451; 568/454
(58) Field of Classification Search ........... 568/429, 568/451, 454
See application file for complete search history.

(56) References Cited

U.S. PATENT DOCUMENTS

| | | | |
|---|---|---|---|
| 4,443,638 A | 4/1984 | Yates ............... 568/882 |
| 4,528,403 A | 7/1985 | Tano et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,059,710 A | 10/1991 | Abatjoglou et al. |
| 5,113,022 A | 5/1992 | Abatjoglou et al. |
| 5,179,055 A | 1/1993 | Wink et al. |
| 5,202,297 A | 4/1993 | Lorz et al. |
| 5,260,491 A | 11/1993 | Wink et al. |
| 5,264,616 A | 11/1993 | Roeper et al. |
| 5,288,918 A | 2/1994 | Maher et al. |
| 5,360,938 A | 11/1994 | Babin et al. |
| 5,710,344 A | 1/1998 | Breikss et al. |
| 5,731,472 A | 3/1998 | Leung et al. |
| 5,767,321 A | 6/1998 | Billig et al. |
| 5,865,957 A * | 2/1999 | Ueda et al. ............. 203/25 |
| 6,015,928 A | 1/2000 | Gubisch et al. |
| 6,184,424 B1 | 2/2001 | Bueschken et al. |
| 6,239,318 B1 | 5/2001 | Schuler et al. |
| 6,265,620 B1 | 7/2001 | Urata et al. |
| 6,331,657 B1 | 12/2001 | Kaizik et al. |
| 6,403,836 B2 | 6/2002 | Kaizik et al. |
| 6,403,837 B1 | 6/2002 | Hess et al. |
| 6,407,295 B1 | 6/2002 | Kaizik et al. |
| 6,440,891 B1 | 8/2002 | Maas et al. |
| 6,482,992 B2 | 11/2002 | Scholz et al. |
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Rottger et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,009,068 B2 | 3/2006 | Schmutzler et al. |
| 7,109,346 B2 | 9/2006 | Beller et al. |
| 2003/0144559 A1 | 7/2003 | Hess et al. |
| 2004/0236133 A1 | 11/2004 | Selent et al. |
| 2004/0238787 A1 | 12/2004 | Wiese et al. |
| 2004/0242947 A1 | 12/2004 | Beller et al. |
| 2005/0043279 A1 | 2/2005 | Selent et al. |

(Continued)

FOREIGN PATENT DOCUMENTS

DE   33 38 340   5/1984

(Continued)

OTHER PUBLICATIONS

U.S. Appl. No. 10/511,280, filed Oct. 22, 2004, Toetsch et al.

(Continued)

*Primary Examiner*—Sikarl A. Witherspoon
(74) *Attorney, Agent, or Firm*—Oblon, Spivak, McClelland, Maier & Neustadt, P.C.

(57) ABSTRACT

Process for preparing aldehydes and alcohols by rhodium-catalyzed hydroformylation of olefins having 6–20 carbon atoms with subsequent separation by distillation of the output from the hydroformylation reaction into the hydroformylation products and a rhodium-containing solution and recirculation of this solution to the hydroformylation reaction, wherein the rhodium concentration of the recirculated rhodium-containing solution is 20–150 ppm by mass.

22 Claims, 1 Drawing Sheet

U.S. PATENT DOCUMENTS

Figure 1:
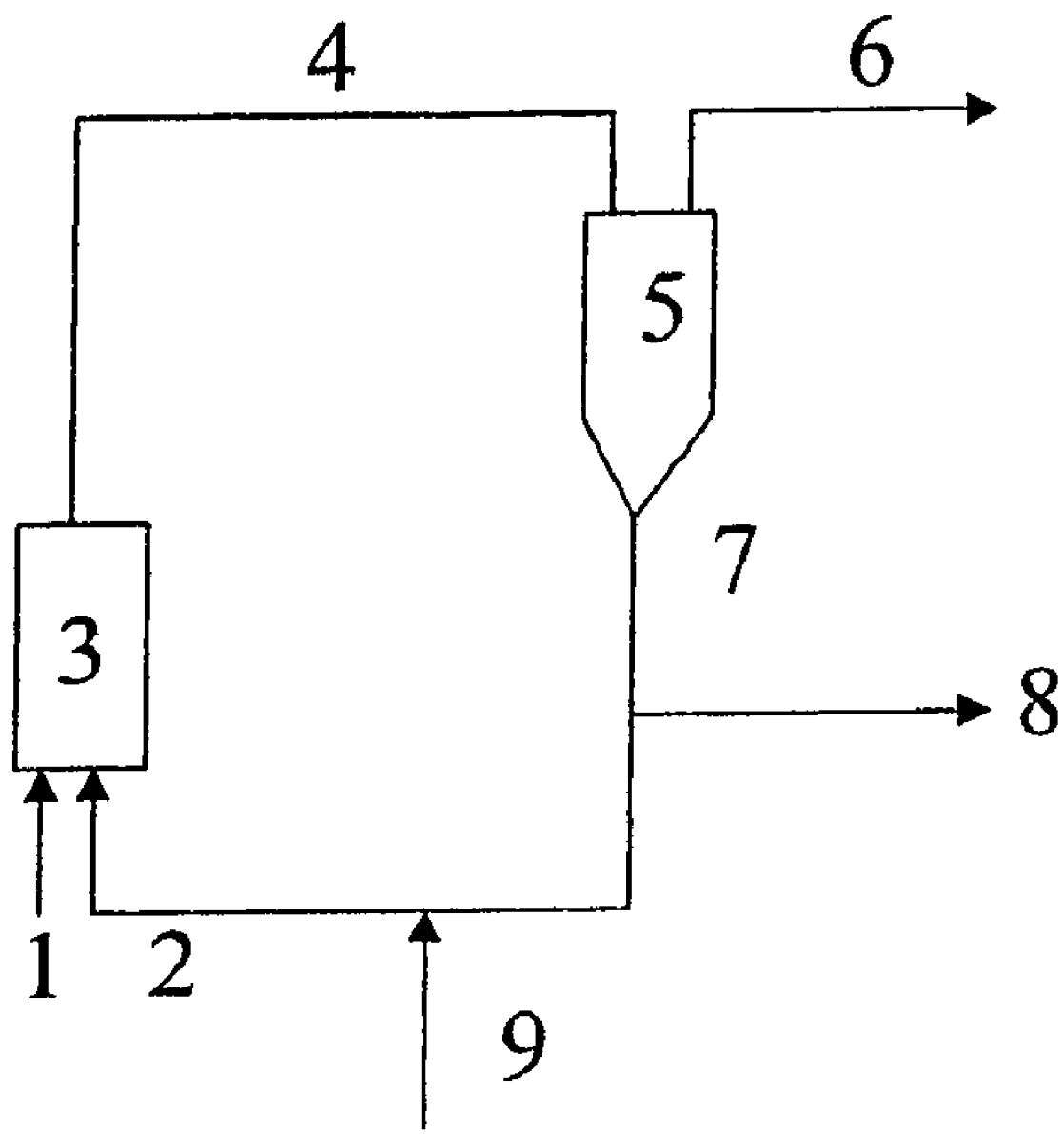

| | | |
|---|---|---|
| 2005/0182277 A1 | 8/2005 | Toetsch et al. |
| 2005/0209489 A1 | 9/2005 | Moller et al. |
| 2005/0234270 A1 | 10/2005 | Kaizik et al. |
| 2005/0256281 A1 | 11/2005 | Grund et al. |
| 2006/0036121 A1 | 2/2006 | Kaizik et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0183936 A1 | 8/2006 | Grass et al. |
| 2006/0241324 A1 | 10/2006 | Moeller et al. |

FOREIGN PATENT DOCUMENTS

| | | |
|---|---|---|
| DE | 198 10 794 | 9/1999 |
| DE | 199 54 510 | 5/2001 |
| DE | 199 54 721 | 5/2001 |
| DE | 100 48 301 | 4/2002 |
| EP | 0 149 894 | 7/1985 |
| EP | 0 155 508 | 9/1985 |
| EP | 0 272 608 | 6/1988 |
| EP | 0 472 071 | 2/1992 |
| EP | 0 518 241 | 12/1992 |
| JP | 63-208540 | 8/1988 |
| JP | 63-218640 | 9/1988 |
| JP | 63-222139 | 9/1988 |
| JP | 7-82281 | 3/1995 |
| JP | 9-268152 | 10/1997 |
| WO | 95/06627 | 3/1995 |
| WO | 97/20795 | 6/1997 |
| WO | 98/43935 | 8/1998 |

OTHER PUBLICATIONS

U.S. Appl. No. 11/494,741, filed Jul. 28, 2006, Kaizik et al.
U.S. Appl. No. 10/562,454, filed Aug. 18, 2006, Krissmann et al.
U.S. Appl. No. 10/576,302, filed Apr. 19, 2006, Kaizik et al.
U.S. Appl. No. 10/588,762, filed Aug. 8, 2006, Wiese et al.
U.S. Appl. No. 10/593,330, filed Sep. 19, 2006, Borgmann et al.
U.S. Appl. No. 10/584,492, filed Jun. 22, 2006, Ortmann et al.
U.S. Appl. No. 10/584,148, filed Jun. 22, 2006, Ortmann et al.

* cited by examiner

METHOD FOR THE RHODIUM-CATALYZED HYDROFORMYLATION OF OLEFINS WITH REDUCTION OF RHODIUM LOSSES

The present invention relates to a process for preparing aldehydes and alcohols by rhodium-catalyzed hydroformylation of olefins, in which the losses of active rhodium catalyst occurring as a result of the work-up of the output from the hydroformylation reaction are minimized.

On an industrial scale, aldehydes and/or alcohols are prepared by hydroformylation of olefins using cobalt or rhodium catalysts. The use of rhodium catalysts is usually advantageous, since they enable higher selectivities and product yields to be achieved. However, rhodium is expensive compared to cobalt, so that the catalyst is a not insignificant cost factor in the hydroformylation of olefins to give the corresponding aldehydes using rhodium catalysts. To improve the economics, the specific catalyst consumption therefore has to be reduced. This is the amount of catalyst which has to be introduced into the process during long-term operation to ensure a constant activity level of the catalyst.

The rhodium-catalyst conversion of olefins into the corresponding aldehydes is usually carried out in a homogeneous, liquid phase. In hydroformylations in a homogeneous phase, i.e. catalyst, olefins, products, solvents, etc., are present in one phase, there is the problem of separating the catalyst from the reaction mixture after the reaction. This can be achieved in a simple fashion by distilling off the unreacted starting material and the products; the catalyst dissolved in the bottoms, usually in high-boiling components, is subsequently returned to the reactor. The distillation can be carried out continuously or batchwise.

Decomposition or deactivation of the catalyst is frequently observed in the separation of the rhodium catalyst from the reaction mixture by distillation. Particularly in the hydroformylation of relatively long-chain olefins, the distillation can only be carried out at elevated temperature and/or under reduced pressure because of the high boiling points of the products, i.e. the conditions required for separating off the catalyst promote its deactivation.

A number of methods of reducing catalyst deactivation during the work-up of the output from the reactor in rhodium-catalyzed hydroformylation reactions of olefins are known:

EP 0272608 describes a process in which a rhodium catalyst comprising triphenylphosphine oxide ligands is used. In the work-up of the reaction mixture, triphenylphosphine is added (in an amount nine times that of the rhodium present), prior to its distillation. The distillation residue thus comprises rhodium complexes having triphenylphosphine as ligands and also triphenylphosphine and triphenylphosphine oxide. The entire, i.e. free and complex, triphenylphosphine is subsequently oxidized to triphenylphosphine oxide and this catalyst solution is returned to the reactor. Oxygen or a peroxide is used for the oxidation of the triphenylphosphine. Further variants of this method are described, for example, in JP 63 222 139, JP 63 208 540, DE 3 338 340 and JP 63 218 640.

These processes have the disadvantage that triphenylphosphine is continually consumed. The equivalent amount of triphenylphosphine oxide is formed from it by oxidation. To limit the concentration of this in the catalyst liquid or in the reactor, a purge stream is necessary, and this in turn results in discharge of rhodium. In addition, an oxidation apparatus is necessary. Unless air is used for the oxidation, the oxidation incurs costs for the oxidant.

To stabilize the phosphorus-containing ligands used for the rhodium, further compounds can be introduced into the hydroformylation reaction and/or the work-up step for the reaction products.

U.S. Pat. Nos. 5,731,472, 5,767,321 and EP 0 149 894 describes processes for the hydroformylation of n-butenes. These processes employ rhodium catalysts which contain phosphite ligands and are stabilized by addition of amines. A disadvantage is that amines can act as catalysts for aldol condensations and thus promote the formation of high boilers.

The hydroformylation in the presence of rhodium complexes as catalysts of a $C_8$-olefin mixture which has been prepared by dimerization of butenes and the stabilization of the complexes by means of substituted phenols are described in JP 04-164042. Here, rhodium compound, ligand and stabilizer are used in a molar ratio of 1/10/50. Disadvantages in this process are the costs for the stabilizer and the expense of separating it off.

The rhodium catalyst is usually recovered as a solution in a high-boiling solvent by distillation of the output from the hydroformylation reaction under mild conditions.

The hydroformylation of olefins in the presence of rhodium catalysts frequently forms small amounts of high boilers as by-products. The high boilers are aldolization and acetalization products and also, as a result of disproportionation of the aldehydes into acids and alcohols, esters of these acids. In the distillation of the output from the hydroformylation, these high boilers remain in the distillation bottoms together with the rhodium compounds. To enable the high boiler concentration in the hydroformylation reactor to be kept at a constant value in a continuous process, an amount of high boilers corresponding to the amount formed, in the hydroformylation reaction has to be separated off in the pseudo-steady state. This is achieved by controlled discharge of part of the distillation bottoms. Proportionate amounts of active rhodium catalyst are also removed from the process circuit in the purge stream. In the ideal case, the amount of rhodium discharged would correspond precisely to that amount of rhodium which would have to be fed in in a continuous process in order to maintain a steady state.

However, in conventional processes, a larger amount of rhodium has to be fed in because insoluble rhodium compounds, e.g. multinuclear rhodium clusters, and/or metallic rhodium are formed during the work-up by distillation as a result of, inter alia, the thermal stress. Although this rhodium continues to be present in the apparatus, it is catalytically inactive and is not available as catalyst in the hydroformylation reactor. Furthermore, the dissolved rhodium compounds present in the bottom product from the distillation, which are returned to the hydroformylation reactor, are less active than a fresh rhodium catalyst, so that even at the same rhodium concentration in the hydroformylation reactor with recirculated rhodium compounds, a lower space-time yield is obtained.

The economics of a hydroformylation process using rhodium catalysts thus depend mainly on the specific rhodium consumption. It is therefore an object of the invention to develop a process for preparing aldehydes by rhodium-catalyzed hydroformylation of olefins which has a low catalyst consumption and can be carried out without addition of catalyst-stabilizing substances.

It has surprisingly been found that the catalyst consumption of a rhodium-catalyzed process for the hydroformylation of olefins can be greatly reduced if particular rhodium concentrations in the distillation bottoms are not exceeded in the work-up of the output from the hydroformylation by distillation.

The present invention accordingly provides a process for preparing aldehydes and alcohols by rhodium-catalyzed hydroformylation of olefins having 6–20 carbon atoms with subsequent separation by distillation of the output from the hydroformylation reaction into the hydroformylation products and a rhodium-containing solution and recirculation of this solution to the hydroformylation reaction, wherein the rhodium concentration of the recirculated rhodium-containing solution is 20–150 ppm by mass.

The rhodium concentration in the recirculated rhodium-containing solution is preferably 20–100 ppm by mass, in particular 20–50 ppm by mass, of rhodium.

To carry out the process of the invention, a number of variants are possible:

FIG. 1 illustrates one variant of the process of the invention. Here, olefin and synthesis gas are fed via line 1 into the hydroformylation reactor 3, and catalyst solution is fed in via line 2. The output from the hydroformylation is conveyed via line 4 to the distillation stage 5 where the desired aldehydes and alcohols are separated off as top product 6. The bottom product 7 comprises the rhodium catalyst and/or high boilers and/or aldehydes and alcohols which have not been separated off and/or inert solvents. Part of the rhodium-containing solution can, if appropriate, be discharged via line 8. The solution is recirculated to the reactor 3, and fresh catalyst can be added via line 9.

Solvents present in the rhodium-containing solution can be the reaction products of the hydroformylation reaction, preferably aldehydes, alcohols and/or high-boilers formed and/or inert solvents such as TEXANOL, dioctyl phthalate (DOP) or diisononyl phthalate (DINP) which have been added. The rhodium concentration is set via the separation by distillation of the output from the hydroformylation reaction, e.g. by means of an appropriate proportion of alcohols and aldehydes. The amount of bottom product can be set by means of appropriate operating conditions of the distillation apparatus (temperature, pressure). As solvents, it is possible to use the high boilers formed in the reaction or added inert solvents, in each case alone or in addition to the alcohols and aldehydes formed in the reaction. If high boilers are not formed in the reaction and no inert solvents are added, the alcohols and aldehydes alone can also serve as solvents.

Inert solvents which can be used are all compounds which have a boiling point sufficiently high to allow the desired aldehydes and alcohols to be separated off and are inert in the hydroformylation reaction and the distillation.

The starting materials for the process of the invention are olefins or olefin mixtures having from 6 to 20 carbon atoms and terminal and/or internal C—C double bonds. The mixtures can comprise olefins having an identical, similar (±2) or significantly different (>±2) number of carbon atoms. Examples of olefins, which can be used as starting material either in pure form, in a mixture of isomers or in admixture with further olefins having a different number of carbon atoms, are: 1-, 2- or 3-hexene, 1-heptene, linear heptenes having an internal double bond (2-heptene, 3-heptene, etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctene, 1-, 2-, 3-, 4- or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond, mixtures of linear hexadecenes. Further suitable starting materials are, inter alia, the mixture of isomeric hexenes formed in the dimerization of propene (dipropene), the mixture of isomeric octenes formed in the dimerization of butenes (dibutene), the mixture of isomeric nonenes formed in the trimerization of propene (tripropene), the mixture of isomeric dodecenes formed in the tetramerization of propene or the trimerization of butenes (tetrapropene or tributene), the hexadecene mixture formed in the tetramerization of butenes (tetrabutene) and also olefin mixtures prepared by cooligomerization of olefins having a different number of carbon atoms (preferably from 2 to 4), if appropriate after fractional distillation to give fractions having an identical or similar (±2) number of carbon atoms. It is also possible to use olefins or olefin mixtures which have been produced by the Fischer-Tropsch synthesis. In addition, olefins which have been prepared by olefin metathesis or by other industrial processes can be used. Preferred starting materials are mixtures of isomeric octenes, nonenes, dodecenes or hexadecenes, i.e. oligomers of lower olefins such as n-butenes, isobutene or propene. Other starting materials which are likewise well suited are oligomers derived from $C_5$-olefins.

Modified rhodium complexes can be used as catalysts in the process of the invention. These rhodium catalysts can be introduced into the process in the form of their active complexes, but it is generally simpler in industry to generate the active catalysts in situ from stable, readily storable rhodium compounds. Rhodium compounds which are suitable for this purpose are, for example, rhodium(II) and rhodium(III) salts such as rhodium(III) chloride, rhodium(III) nitrate, rhodium(III) sulfate, potassium rhodium sulfate, rhodium(II) or rhodium(III) carboxylates, rhodium(II) and rhodium(III) acetate, rhodium(II) octanoate, rhodium(II) nonanoate, rhodium(III) oxide, salts of rhodic(III) acid, trisammonium hexachlororhodate(III). Also suitable are rhodium complexes such as dicarbonylrhodium acetylacetonate, acetylacetonatobis-ethylenerhodium(I) Particularly useful compounds are rhodium acetate, rhodium octanoate and rhodium nonanoate.

In general, about 1–500 and preferably 3–50 mol of ligand is used per mole of rhodium. Fresh ligand can be added to the reaction at any point in time to keep the concentration of free ligand constant.

In the process of the invention, the concentration of rhodium in the hydroformylation reactor is preferably from 1 to 50 ppm by mass, in particular from 5 to 25 ppm by mass.

The choice of ligands added is not restricted in the process of the invention, but depends on the olefin used and on the desired products. Preferred ligands are ligands containing nitrogen, phosphorus, arsenic or antimony atoms, and particular preference is given to phosphorus ligands. The ligands can be monodentate or polydentate, and in the case of chiral ligands, it is possible to use either the racemate or one enantiomer or diastereomer. It is likewise possible to use a mixture of two or more different ligands. As phosphorus ligands, particular preference is given to using those which form complexes with rhodium which are less stable than the triphenylphosphine complexes, for example phosphine oxides, phosphites, phosphonites and phosphinites.

Examples of phosphites are trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl) phosphite, triphenyl phosphite, tris(2,4-di-t-butylphenyl) phosphite, tris(2-t-butyl-4- methoxyphenyl) phosphite, tris(2-t-butyl-4-methylphenyl), phosphite, tris(p-cresyl) phosphite. Further suitable phosphites are sterically hindered phosphite ligands which are described, for example, in EP 155 508, U.S. Pat. Nos. 4,668,651, 4,748,261, 4,769,498, 4,774,361, 4,835,299, 4,885,401, 5,059,710, 5,113,022, 5,179,055, 5,260,491, 5,264,616, 5,288,918, 5,360,938, EP 472 071, EP 518 241 and WO 97/20795. Preference is given to using triphenyl phosphites which are substituted by 1 or 2 isopropyl and/or tert-butyl groups on the phenyl rings, preferably in the ortho position relative to the phosphite ester group. Examples of phosphonites are methyldiethoxyphosphine, phenyldimethoxyphosphine, phenyldiphenoxyphosphine, 6-phenoxy-6H-dibenz[c,e][1,2]oxaphosphorin and their derivatives in which all or some of the hydrogen atoms are replaced by alkyl or aryl radicals or halogen atoms, and also the ligands described in the patents WO 9843935, JP 09-268152 and DE 198 10 794 and in the German patent applications DE 199 54 721 and DE 199 54 510.

Customary phosphinite ligands are described, for example, in U.S. Pat. No. 5,710,344, WO 95 06627, U.S. Pat. No. 5,360,938, JP 07082281. Examples are diphenyl (phenoxy)phosphine and its derivatives in which all or some of the hydrogen atoms are replaced by alkyl or aryl radicals or halogen atoms, and diphenyl(methoxy)phosphine, diphenyl(ethoxy)phosphine, etc.

In the process of the invention, the rhodium-catalyst hydroformylations are carried out at pressures of from 15 to 300 bar, preferably at pressures of from 15 to 270 bar, in particular at pressures of 150–270 bar. The pressure employed depends on the structure of the starting olefins, the rhodium catalyst used and the desired effect. Thus, for example, α-olefins can be converted into the corresponding aldehydes in high space-time yields at pressures below 64 bar. On the other hand, in the case of olefins having internal double bonds, in particular branched olefins, higher pressures are advantageous.

The temperatures for the rhodium-catalyzed, hydroformylations according to the invention are generally in the range from 40° C. to 180° C., preferably from 90° C. to 160° C., in particular from 130 to 160° C.

After the hydroformylation, the major part of the synthesis gas is removed by reducing the pressure. The catalyst is separated off from the liquid reaction output by distillation. The catalyst and any added ligands, stabilizers, etc., remain in/as the distillation residue. During start-up, or if only a small amount of high boilers is formed in the process, it may be advantageous to use a high-boiling inert solvent (i.e. a solvent having a higher boiling point than the products and starting materials) in which the catalyst dissolves. The catalyst dissolved in the high-boiling solvent can then be recirculated directly to the reactors. It is particularly advantageous to use the high-boiling by-products formed in the process as high-boiling solvent. Other suitable solvents are high-boiling esters such as 2,2,4-trimethylpentane-1,3-diol monoisobutyrate, which is commercially available as TEXANOL.

Various procedures can be employed industrially to separate off the catalyst by distillation. The catalyst solution is preferably separated off by means of falling film evaporators, short-path evaporators or thin film evaporators or combinations of these apparatuses. The advantage of such combinations can be, for example, that synthesis gas still dissolved in the mixture and part of the products and the starting olefins still present can be separated off in a first step (for example in a falling film evaporator) and the catalyst can then be separated off in a second step (for example in a thin film evaporator).

The distillation pressures are in the range from 5 mbar to 1 bar, preferably from 10 mbar to 100 mbar. The distillation temperatures are from 40 to 180° C., in particular from 80 to 150° C.

The rhodium-containing solution (bottom product) can, if desired, be additionally stabilized with carbon monoxide, as described in DE 100 48 301.1.

Part of the rhodium-containing solution (bottom product) can be discharged to maintain a constant high boiler concentration in the hydroformylation reactor. The other part of the bottom product is recirculated to the hydroformylation reactor. Part of the catalyst (rhodium and ligand) is removed from the process with the purge stream. These amounts and other deficits of rhodium and ligand in the recirculated stream have to be replaced to maintain a given catalyst concentration in the hydroformylation reactor. In the ideal case, only these amounts of rhodium catalyst need to be replaced.

If appropriate, further products can be separated off from the purge stream, for example by distillation.

The rhodium can be recovered from the purge stream by known methods.

The vapor obtained in the concentration step can be separated by distillation into the target products, aldehydes and alcohols, hydrocarbons and other by-products. If appropriate, olefins can be recovered from the hydrocarbon fraction and recirculated to the process.

The aldehydes obtained by means of the process of the invention can be used as such, for example as fragrances, can be oxidized to carboxylic acids or can be hydrogenated to give alcohols.

The alcohols formed in the process of the invention or the alcohols obtained by hydrogenation of the aldehydes are precursors for esters, in particular plasticizers, for example phthalates, hydrophthalates, adipates, citrates, trimellitates, and for detergents. Furthermore, they can be used as solvents.

The following examples illustrate the invention without restricting its scope, which is defined by the description and the claims.

EXAMPLE 1

Rhodium-Catalyzed Hydroformylation of C12-Olefin (Tributene) Using Fresh Catalyst In a 10 l autoclave, 5000 g of tributene from the Octol process were reacted at 135° C. under a synthesis gas pressure of 250 bar in the presence of a phosphite-modified rhodium catalyst for 4 hours. The active rhodium catalyst was generated in situ from rhodium octanoate and tris(2,4-di-tert-butylphenyl) phosphite. The rhodium concentration (based on the total reaction mixture) was set to 10 ppm, and the molar phosphorus/rhodium ratio (P/Rh) was 10:1.

As inert, high-boiling solvent, 250 g of TEXANOL (2,2,4-trimethylpentane-1,3-diol monoisobutyrate) were added to the reaction mixture.

The conversion of the olefin was monitored both by means of GC analysis and via the amount of synthesis gas taken up. After 4 hours, the reaction was stopped. The crude reaction product mixture comprised 16.5% by mass of C12-olefin, 78.1% by mass of C13-aldehyde (isotridecanal), 4.3% by mass of C13-alcohol (isotridecanol) and 1.1% by mass of high boilers. This product composition corresponds to a tributene conversion of 81.2% and a yield of desired products (C13-aldehyde/-alcohol) of 79.7%.

EXAMPLE 2

Comparative Example

Rhodium Recovery from the Crude Reaction Product Mixture

For the recovery of the catalyst, 2500 g of the crude reaction product mixture from Example 1 were fractionated in a laboratory thin film evaporator at 130° C. and 20 mbar. In this procedure, the rhodium-containing high boiler was separated off from the low boilers (desired products, unreacted C13-olefin). Under the separation conditions chosen, a rhodium-containing high boiler (bottom product) having a rhodium content of 248 ppm was obtained at the bottom of the thin film evaporator.

EXAMPLE 3

According to the Invention

Rhodium Recovery from the Crude Reaction Product Mixture

As in Example 2, 2500 g of the crude reaction product mixture from Example 1 were treated in a laboratory thin film evaporator at 130° C. and 40 mbar to recover the catalyst. In this procedure, the rhodium-containing high boiler was separated off from the low boilers (desired products, unreacted C13-olefin). Under the milder (compared to Example 2) separation conditions, a rhodium content of 43 ppm was achieved in the bottom product.

EXAMPLE 4

Comparative Example

Hydroformylation of C12-Olefin (Tributene) Using Recycled Catalyst

In a 2 l autoclave, 1000 g of tributene from the Octol process were reacted at 135° C. under a synthesis gas pressure of 250 bar in the presence of a recycled, used rhodium catalyst for 4 hours. As catalyst precursor, use was made of the highly concentrated rhodium-containing high boiler containing 248 ppm of rhodium obtained in Example 2. The rhodium-content (based on the total reaction mixture) was set to 10 ppm, as in Example 1. The molar phosphorus/rhodium ratio (P/Rh) was 10:1.

The conversion of the olefin was monitored both by means of GC analysis and via the amount of synthesis gas taken up. After a time of 4 hours, a tributene conversion of 67.3% and a yield of desired product (C13-aldehyde/-alcohol) of 66.2% were determined. Compared to the use of fresh rhodium catalyst (Example 1), a significant decrease in the conversion and the yield of desired product is found when the used catalyst is employed.

EXAMPLE 5

According to the Invention

Hydroformylation of C12-Olefin (Tributene) Using Recycled Catalyst

In a 2 l autoclave, 1000 g of tributene from the Octol process were reacted at 135° C. under a synthesis gas pressure of 250 bar in the presence of a recycled, used rhodium catalyst for 4 hours. As catalyst precursor, use was made of the rhodium-containing high boiler from Example 3, which at 43 ppm of rhodium had a lower rhodium concentration than that from Example 2. The rhodium content (based on the total mixture) was set to 10 ppm, as in Examples 1 and 4. The molar phosphorus/rhodium ratio (P/Rh) was 10:1.

The conversion of the olefin was, as in Examples 1 and 3, monitored both by means of GC analysis and via the amount of synthesis gas taken up. After a time of 4 hours, a tributene conversion of 80.5% and a yield of desired product (C13-aldehyde/-alcohol) of 79.0% were determined. Compared to the use of fresh catalyst (Example 1), no appreciable decrease in the conversion and the yield of desired product is observed when the used catalyst prepared from less concentrated rhodium-containing high boilers containing 43 ppm of Rh is employed.

The invention claimed is:

1. A process for preparing aldehydes and alcohols comprising:
    subjecting olefins having 6–20 carbon atoms to a rhodium-catalyzed hydroformylation at an initial concentration of rhodium,
    distilling the output from the hydroformylation, whereby hydroformylation products and a rhodium-containing solution are separated from said output, while setting the rhodium concentration of the rhodium-containing solution to 20–150 ppm by mass, and
    recirculating said rhodium-containing solution, whereby the concentration of rhodium in the recirculated rhodium-containing solution is adjusted to an initial concentration of rhodium.

2. The process as claimed in claim 1, wherein the rhodium-containing solution comprises the reaction products of the hydroformylation reaction as solvent and the recirculated rhodium concentration is set by means of the separation by distillation of the output from the hydroformylation reaction.

3. The process as claimed in claim 1, wherein the rhodium-containing solution comprises an inert solvent as solvent and the recirculated rhodium concentration is set by means of the separation by distillation of the output from the hydroformylation reaction.

4. The process as claimed in claim 1, wherein the rhodium-containing solution comprises the high boilers, aldehydes and alcohols formed in the hydroformylation reaction as solvent and the recirculated rhodium concentration is set by means of the proportion of aldehydes and alcohols via the separation by distillation of the output from the hydroformylation reaction.

5. The process as claimed in claim 1, wherein the rhodium-containing solution comprises the aldehydes and alcohols formed in the hydroformylation reaction and an inert solvent as solvents and the recirculated rhodium concentration is set by means of the proportion of aldehydes and alcohols via the separation by distillation of the output from the hydroformylation reaction.

6. The process as claimed in claim 5, wherein 2,2,4-trimethylpentane-1,3-diol monoisobutyrate, dioctyl phthalate or diisononyl phthalate is used as inert solvent.

7. The process as claimed in claim 1, wherein the rhodium catalysts comprise phosphite ligands.

8. The process as claimed in claim 7, wherein the rhodium catalysts comprise tris (2,4-di-t-butylphenyl) phosphite as ligand.

9. The process as claimed in claim 2, wherein the rhodium-containing solution comprises the high boilers, aldehydes and alcohols formed in the hydroformylation reaction as solvent and the recirculated rhodium concentration is set by means of the proportion of aldehydes and alcohols via the separation by distillation of the output from the hydroformylation reaction.

10. The process as claimed in claim 2, wherein the rhodium-containing solution comprises the aldehydes and alcohols formed in the hydroformylation reaction and an inert solvent as solvents and the recirculated rhodium concentration is set by means of the proportion of aldehydes and alcohols via the separation by distillation of the output from the hydroformylation reaction.

11. The process as claimed in claim 3, wherein the rhodium-containing solution comprises the aldehydes and alcohols formed in the hydroformylation reaction and an inert solvent as solvents and the recirculated rhodium concentration is set by means of the proportion of aldehydes and alcohols via the separation by distillation of the output from the hydroformylation reaction.

12. The process as claimed in claim 10, wherein 2,2,4-trimethylpentane-1,3-diol-monoisobutyrate, dioctyl phthalate or diisononyl phthalate is used as inert solvent.

13. The process as claimed in claim 11, wherein 2,2,4-trimethylpentane-1,3-diol-monoisobutyrate, dioctly phthalate or diisononyl phthalate is used as the inert solvent.

14. The process as claimed in claim 2, wherein the rhodium catalysts comprise phosphite ligands.

15. The process as claimed in claim 3, wherein the rhodium catalysts comprise phosphite ligands.

16. The process as claimed in claim 4, wherein the rhodium catalysts comprise phosphite ligands.

17. The process as claimed in claim 5, wherein the rhodium catalysts comprise phosphite ligands.

18. The process as claimed in claim 6, wherein the rhodium catalysts comprise phosphite ligands.

19. The process as claimed in claim 1, wherein the rhodium concentration of the recirculated rhodium-containing solution is 20–100 ppm by mass.

20. The process as claimed in claim 1, wherein the rhodium concentration of the recirculated rhodium-containing solution 20–50 ppm by mass.

21. The process as claimed in claim 1, wherein the hydroformylation is carried out at a pressure in the range of 150 to 270 bar.

22. The process as claimed in claim 1, wherein recirculation of the solution to the hydroformylation reaction is carried out without subjecting said solution to an oxidation.

* * * * *